United States Patent [19]
Klokkers et al.

[11] Patent Number: 6,022,852
[45] Date of Patent: Feb. 8, 2000

[54] PHARMACEUTICAL COMPOSITION CONTAINING CYCLOSPORIN A

[75] Inventors: Karin Klokkers; Wilfried Fischer, both of Holzkircher, Germany

[73] Assignee: Hexal AG, Holzkirchen, Germany

[21] Appl. No.: 09/076,175

[22] Filed: May 11, 1998

Related U.S. Application Data

[63] Continuation-in-part of application No. 08/633,823, Jun. 27, 1996, abandoned.

[30] Foreign Application Priority Data

Oct. 22, 1993 [DE] Germany .............................. 43 36 163

[51] Int. Cl.$^7$ ......................... A61K 38/00; A61K 31/355
[52] U.S. Cl. .............................................. 514/11; 514/458
[58] Field of Search ........................................ 514/11, 458

[56] References Cited

U.S. PATENT DOCUMENTS 5,430,021  7/1995  Rudnic et al. ............................. 514/14

OTHER PUBLICATIONS

Sokol et al., "Improvement of cyclosporin absorption in children after liver transplantation by means of water–soluble vitamin E", vol. 228, pp. 212–215, Jul. 1991.

*Primary Examiner*—Raymond Henley, III
*Attorney, Agent, or Firm*—Cohen, Pontani, Lieberman & Pavane

[57] ABSTRACT

The invention relates to a pharmaceutical composition consisting of or containing cyclosporin A and α-tocopherol or one of the derivatives thereof.

6 Claims, No Drawings

PHARMACEUTICAL COMPOSITION CONTAINING CYCLOSPORIN A

RELATED APPLICATIONS

This application is a continuation-in-part of application Ser. No. 08/633,823, filed Jun. 27, 1996, now abandoned.

BACKGROUND OF THE INVENTION

1. Field of the Invention

The invention relates to pharmaceutical compositions containing an effective amount of cyclosporin A in combination with vitamin E, vitamin E derivatives or vitamin E concentrates in which natural vitamin E is present together with vegetable-oil components.

2. Prior Art

Cyclosporin A is a cyclic, water-insoluble, non-polar undecapeptide. The compound is an effective immunosuppressant obtained from fungal cultures (Cane et al., Transplant TROC. 13: 349–358 (1981); Ferguson et al., Surgery 92: 175–182 (1952)). The medicament is used to prevent the rejection of transplanted allogeneic organs (Bennett & Norman, Arzn. Rev. Med. 37, 215–224 (1936); Van Basen, Surg. Clin. North Am. 66. 435–449 (1986)). Its immunosuppressive action is based on selective inhibition of cell function which allows the survival of, for example, heart transplants, without myelocyte suppression (Myers et al., New England journal of Medicine 311: 699 (1994)). In addition to its use in transplantation, more recent clinical trials have shown that cyclosporin A is effective in the treatment of a large number of autoimmune diseases. For example, clinical trials of the treatment of polymyositis, systemic lupus erythematosus, rheumatoid arthritis or even of early-onset insulin-dependent diabetes have been carried out (see the corresponding chapter in: Cyclosporine in Autoimmune Diseases, ed. Schindler, Springer Verlag, Berlin 1985).

Cyclosporin is a lipophilic molecule having a molecular weight of 1202 daltons. Owing to the poor solubility in water and the high lipophilicity of cyclosporin A, pharmaceutical compositions of cyclosporin A with customary solid or liquid pharmaceutical carriers often have disadvantages. For example, the cyclosporins are not satisfactorily absorbed from such compositions (Cavanak & Sucker, Formulation of Dosage Forms, Prog. Allergy 38, 65–72 (1956)), or the compositions are not well tolerated, or they are not sufficiently stable when stored, for example with regard to crystallising out of the cyclosporin. Often the dissolved concentration is low in relation to the daily dose of up to 1 g, for example only 3%, which means that 30 g of solution have to be taken. Greater solubility is indicated in DE-B-2 907 460 wherein a solution of cyclosporin in vegetable oil, such as olive oil or corn oil, ethanol and an emulsifier consisting of a non-ionic ester of a triglyceride with a polyalkylene glycol is described. Examples of the compositions indicated in that patent as being preferred are drinkable solutions, drinkable emulsions, injection solutions and solutions in capsules.

The above composition is administered preferably intramuscularly, or subcutaneously, or especially orally. Cyclosporin A administered in the above medicament forms is distinguished by good bioavailability. Once it has been absorbed, the substance binds rapidly to plasma proteins and has a terminal half-life of 24 hours. A high percentage thereof is metabolized in the liver, biliary excretion being the main elimination route (Beverige, Cyclosporin A, in: Proceedings of International Symposium, Cambridge, ed. White, pages 35–44 (1982).

Despite its great value as an immunosuppressant, the clinical use of cyclosporin is limited by the main side effect of chronic administration which is the nephrotoxicity of the active ingredient itself (Van Buren, Surg. Clin. North Am. 66, 435–449 (1986)). In addition, renal toxicity occurs in approximately 80% of kidney transplant patients (Kahan, Dial. Transplant. 12: 620–630 (1983)) as a result of the very side effect immanent in the substance which is used to protect the transplant against rejection.

Frequent side effects of cyclosporin treatments in various autoimmune diseases include nephrotoxicity, hypertension, hyperkalaemia, hyperuricaemia, hepatotoxicity, anaemia, hypertrichosis, gingival hyperplasia, gastrointestinal side effects, tremors and paraesthesia (Von Graffenried et al., Cyclosporine in Autoimmune Diseases, ed. Schindler, Springer Verlag, Berlin, pages 59–73 (1985)). Of the side effects quoted here, nephrotoxicity is the most frequent. Acute, cyclosporin-induced nephrotoxicity is dosage-dependent and correlates with the cyclosporin blood levels. It is reversible after a reduction in dosage or when the cyclosporin treatment has been completed (Chapman et al., Lancet I: 128 (1985)).

Acute cyclosporin nephrotoxicity is accompanied morphologically by tubular lesions characterised by inclusion bodies, isometric vacuolation and microcalcification (Mihatsch et al., Transplant. Proc. 15: 2821 (1983)). That leads to a decrease in the glomerular filtration rate, which can be identified by the rapid increase in serum creatinine in patients treated with cyclosporin. One reason could be disturbance of the microcirculation as a result of the interaction of cyclosporin with local prostacyclin synthesis (Neild et al., in: Cyclosporine, ed. Kahan, Gruen & Stratton, Orlando, Fla., page 182 (1984)).

Although the mechanism of renal dysfunction is not yet fully explained, it has been shown that renal synthesis of thromboxane occurs during the progression of immuno-mediated and non-immuno-mediated models of renal damage (Lianos et al., J. Clin. Invest. 72: 1439–1448 (1983): Okegawa et al., J. Clin. Invest. 71: 81–90 (1983)). Thromboxane is a prostanoid and hence a metabolite of arachidonic acid from the cyclo-oxygenase cycle. The other prostanoids are prostaglandins and prostacyclins. Prostanoids are very effective mediators that are formed during immunologically generated inflammation processes. They can fundamentally alter the renal haemodynamics (Morley, in: Lymphokines, ed. Pic, Academic Press, New York, 4: 377–391 (1981)).

EP-A-0 305 400 describes the connections between disturbed prostanoid synthesis and nephrotoxicity. According to that specification, the administration of cyclosporin is accompanied by increased synthesis of thromboxane B2, a mediator of inflammation. Cyclosporin is accordingly said also to promote the formation of prostaglandins of the E series, which are likewise inflammation mediators. The rejection of human kidney transplants was linked to a rapid increase in renally eliminated thromboxane B2.

EP-A-0 035 400 also describes the use of ω3-unsaturated fatty acids in combination with cyclosporin A in the inhibition of prostaglandin or thromboxane formation.

A disadvantage of longer-term administration of ω3-fatty acids is the development of vitamin E deficiency states. Symptoms of deficiency are, for example, haemolysis and a reduction in the life of erythrocytes. In animal experiments, vitamin E deficiency leads to degenerative muscle changes, creatinuria and increased haemolysis of erythrocytes and affects certain hormones and enzymes and the metabolism of proteins and arachidonic acid (Machlin, Vitamin E, in: Machlin, Handbook of Vitamins: Nutritional, Biochemical and Clinical Aspects, pages 99–145. Marcel Dekker, New York, 1984)

A further disadvantage of the composition containing ω3-unsaturated fatty acids (fish oils) is the concentration, obviously low, of active ingredient that can be achieved in that oil. For example, EP-A-0 305 400 described a concentration of only 12.5 mg of cyclosporin A per gram of fish oil. At a customary daily dose of more than 300 mg of cyclosporin A, that means a total intake of approximately 24 grams of preparation, at 1 g of cyclosporin A per 80 g of preparation. That is an unacceptably large amount of oil for a patient; for example, encapsulated in soft gelatin capsules, it would mean a daily intake of 24 capsules containing 300 mg of cyclosporin A. Parenteral administration by infusion would, in the case of an infusion emulsion containing, at an optimistic estimate, 10% oil, involve an amount of approx. 240 ml of emulsion containing 300 mg of cyclosporin A, a volume that can be infused only over a relatively long period of time. Both features militate totally against the chronic administration required in the case of transplant patients.

Although the formulations according to DE-B-2 907 460 are distinguished by their large dissolving capacity for cyclosporin A, they have the disadvantage that they comprise only vegetable oils, which do not contain any substances that inhibit prostaglandin or thromboxane synthesis. That means that those preparations do not inhibit the nephrotoxicity of the cyclosporin A. The commercially available parenteral solution of cyclosporin A (Sandimmun®, made by Sandoz) contains, in 1 ml of solution, 50 mg of cyclosporin A, 32.9% ethanol and 650 mg of Cremeopher EL, an ethoxylated, hydrogenated castor oil. In addition to the amount of 2 g of ethanol per application, which represents a burden for the liver, according to reports in the literature Cremeopher EL is nephrotoxically similar to cyclosporin A itself (Thiel et at., Clin. Nephrol. 25 (Suppl. 1), 540–542 (1986); Finn et al., Renal Failure 11, 3–15 (1989)). For example, in isolated, perfused rat kidney, Cremeopher EL leads to marked renal vasoconstriction with reduced renal blood flow and tubular dysfunction (Besarab et al., Transplantation 44, 195–201 (1987) Luke et al., Transplantation 43, 795–799 (1987)). Furthermore, Cremeopher EL causes anaphylactic reactions, which may be as severe as anaphylactic shock (Chapuis et al., Engl. J. Med. 312, 1259 (1985), Leunissen et al., Lancet 1, 637 (1986): Magalini et al., Transplantation 42, 443–444 (1986)). Cremeopher EL is regarded as the cause of the anaphylactoid reaction as it leads to histamine liberation (Ennis et al., Agents Action 12, 64–80 (1982)). In some cases of therapy using the i.v. solution, the allergic reaction was observed in humans on the first administration (Friedman et al., Am. J. Med. 78, 343–345 (1985); Magalini et al., Transplantation 42, 443–444 (1986)). A disadvantage of the commercially available parenteral preparation is accordingly the constituent Cremeopher EL. Efforts should be made to obtain a formulation that does not contain that excipient, in order to avoid the above side effects and to increase the safety of the medicament.

The advantageous immunosuppressive properties of cyclosporin A are exploited in the treatment of psoriasis. Owing to its high molecular weight and its very high degree of lipophilicity, cyclosporin A is not, however, capable of penetrating intact skin, especially the horny layer. For that reason, severe cases of psoriasis are treated with oral and parenteral administration of cyclosporin. Disadvantages of such administration are the systemic side effects on the circulation (hypertension) and kidney function. Topical preparations for the treatment of psoriasis, which would reduce the systemic side effects, require absorption promotors, such as, for example, propylene glycol and azone (Duncan et al., British Journal of Dermatology 123: 631–640 (1990)). It is, however, known that the permeation-promoting properties of azone are attributable to disturbance, or even destruction, of the protective function of the horny layer. Propylene glycol leads to drying-out of the skin. The two substances would therefore hinder rather than assist the healing of the psoriasis. For that reason a topical preparation containing a therapeutically adequate amount of cyclosporin A in combination with substances that assist the healing process would be desirable. In addition, the combination should promote the permeation of cyclosporin A through intact skin.

3. THE PROBLEM OF THE INVENTION

The problem of the present invention is to find an advantageous solvent system that dissolves cyclosporin A in sufficient quantities for it to be taken orally in the therapeutically customary daily dose; that is capable of reducing nephrotoxic activity; that, when applied topically, is capable both of promoting permeation through the skin and of assisting the healing process in the treatment of psoriasis and that, in addition, ensures parenteral administration that is well tolerated.

4. SUMMARY OF THE INVENTION

The problem underlying the invention is solved by a pharmaceutical preparation that consists of or contains cyclosporin A and α-tocopherol or one of the derivatives thereof.

That pharmaceutical preparation can be characterised by α-tocopherol succinate, α-tocopherol acetate or D-α-tocopherol polyethylene glycol 1000 succinate as the α-tocopherol derivative.

The pharmaceutical preparation can be characterised further by the fact that it contains α-tocopherol in the form of an α-tocopherol concentrate in vegetable oil.

The pharmaceutical preparation is obtainable by mixing cyclosporin A with an α-tocopherol concentrate in vegetable oil.

The pharmaceutical preparation can also be characterised by the fact that it contains α-tocopherol or one of the derivatives thereof in an amount of up to 900%, based on cyclosporin A.

The pharmaceutical preparation can also be characterised by the fact that it contains cyclosporin A in an amount of ≧10%, based on the composition.

The pharmaceutical preparation can also be characterised by the fact that it contains ethanol or isopropanol as processing auxiliary, especially in amounts of up to 20%.

The pharmaceutical preparation can also be characterised by the fact that it contains an emulsifier.

The pharmaceutical preparation can also be characterized by the fact that it contains a thickener.

The pharmaceutical preparation can, finally, be provided in the form of an injection concentrate for formulations for parenteral use containing physiologically tolerable excipients customary therefor.

DESCRIPTION OF THE PREFERRED EMBODIMENTS

According to the invention, it has also been found, surprisingly, THAT α-tocopherol and its chemical derivatives, such as α-tocopherol succinate and D-α-tocopherol polyethylene glycol 1000 succinate and α-tocopherol acetate, but especially highly concentrated concentrates of D-α-tocopherol in vegetable oils, have an excellent dissolving capacity for cyclosporin A, at the same time inhibit the synthesis of prostanoids, such as prostaglandins and thromboxanes, which can be exploited to reduce nephrotoxicity and to cause inflammation reactions in the skin to subside, and at the same time promote the absorption of cyclosporin A through intact skin. In addition, solutions according to the invention, optionally with the assistance of physiologically tolerable customary excipients for the preparation of formulations for parenteral use, can be formulated as injection concentrates. The special advantage of the solutions according to the invention, in addition to the achievement of high concentrations of dissolved cyclosporin A of more than 10%, is that D-α-tocopherol, as natural vitamin E, and its derivatives have inherent effects which on the one hand counteract toxic effects of cyclosporin A at the customary high doses used in the case of oral and parenteral administration and on the other hand reinforce the intended immunosuppressive effect in the ease of the topical treatment of psoriasis by means of their absorption-promoting effect.

For example vitamin E affects the metabolism of arachidonic aid by inhibiting prostaglandin, thromboxane and leucotriene biosynthesis and increasing prostacyclin formation. Those properties are associated with biological inhibition of inflammation and with thrombotic disorders (Machlin, Vitamin E, in: Machlin, Handbook of Vitamins: Nutritional, Biochemical and Clinical Aspects, pages 99–145, Marcel Dekker, New York, 1984). When taken orally, vitamin E can likewise promote the activity of non-steroidal anti-inflammatory medicaments (Bertolini et al., Rivista di Pharmakologia et Therapia 8, pages 27–34 (1982); Klein & Blankenhorn, Vergleich der klinischen Wirksamkeit von Vitamin E und Diclofenac Natrium bei Spondylitis Ancylosans (Morbus Bechterew), Vitaminspur 2, pages 137–142 (1987)). When applied topically, vitamin E permeates the horny layer very well. Quantitative absorption studies have been carried out on the skin of experimental animals. For example, 16 hours after the application of 300 μg of a 5% vitamin E solution in ethanol per $cm^2$, 0.7% of the vitamin E; was recovered in the horny layer and approx. 40.9% in layers of skin below the horny layer (Djerassi et al., Vitamin E: Biochemical function and its role in cosmetics, Drug & Cosmetic Industry 13: No. 1, pages 29–31, 34, 78 (1986)). When applied locally, vitamin E acts as a membrane-stabilising antioxidant and inhibits the liberation of histamine and hydrolytic enzymes, for example from mast cells and lysosomes by stabilising the membranes thereof. Likewise, it inhibits the synthesis of certain prostaglandins, deactivates oxygen radicals and detoxifies corresponding secondary products (Sies, Bildung, von Superoxidradikalen und Peroxiden, in: Superoxiddismutase—Biocthemie und therapeutscher Einsatz; ed. Puhl & Ries, Perimed Verlag, Erlangen, 1982). In addition, vitamin E increased skin moisture and acts as a quasi-occlusion agent. All of those properties that have been described are advantageous in the treatment of psoriasis.

Cyclosporin A dissolves, entirely unexpectedly, in vitamin E preparations, such as vitamin E concentrates (Copherol F 1300), in a high concentration of >10%, with the result that a combination thereof in the form of a solution can be used to therapeutic effect both in soft gelatin capsules and in topical formulations. In order to assist their proccessability, the formulations may contain small amounts of alcohol, such us ethanol or isopropanol in amounts of up to 20% of the total formulation, and, in order to promote wetting, may contain physiologically tolerable surface-active substances, i.e. emulsifiers. Emulsifiers that are tolerable both orally and topically are, for example, phospholipids, such as lecithins, lysolecithins, ethoxylation products of fatty acids and fats, alkali soaps, sucrose esters and others, but are not limited thereto. In addition, the formulations may contain thickeners, such as colloidal silica or polyacrylic acid or polyacrylic acid derivatives or cellulose derivatives and antioxidants and flavour enhancers.

5. EXAMPLES

Example 1

Composition for a Soft Gelatin Capsule

| | |
|---|---|
| cyclosporin A | 100 mg |
| tocopherol (Copberol F1300) | 900 mg |

Example 2

Composition for a Soft Gelatin Capsule

| | |
|---|---|
| cyclosporin A | 100 mg |
| ethanol | 100 mg |
| soya lecithin | 200 mg |
| tocopherol (Copherol F1300) | 600 mg |

Example 3

Composition for a Soft Gelatin Capsule

| | |
|---|---|
| cyclosporin A | 125 mg |
| abs. ethanol | 125 mg |
| D-α-tocopherol | 325 mg |
| D-α-tocopherol ethylene glycol 1000 succinate | 425 mg |

Example 4

Topical Preparation

| | |
|---|---|
| cyclosporin A | 10 mg |
| tocopherol (Copberol F1300) | 90 mg |
| lecithin | 100 mg |
| isopropanol | 200 mg |
| polyacrylic acid | 15 mg |
| triethanolamine | 5 mg |
| water ad | 1000 mg |

Example 5

Injection Concentrate

| | |
|---|---|
| cyclosporin A | 50 mg |
| tocopherol (Copherol F1300) | 100 mg |
| lecithin | 200 mg |
| ethanol | 100 mg |
| eutanol | 500 mg |

Example 6

Test (Hard Gelatine Capsules)

The composition of the formulation was as follows:

| | |
|---|---|
| Cyclosporin A | 100 mg |
| Ethanol 96% | 200 mg |
| Tocopherol PEG 100 succinate | 300 mg |
| Polyethoxylated castor oil | 200 mg |
| Polyethylene glycol 400 (PEG 400) | 200 mg |

This mixture was filled into hard gelatine capsules and tested with dogs in a cross-over test in comparison to a product of the market, i. e. Sandimmun (Optival®). Plasma levels were analyzed by means of a fluorescence immuno essay.

We claim:

1. Pharmaceutical preparation comprised of cyclosporin A, tocopherol polyethylene glycol 1000 succinate and optionally an emulsifier, with the exception of vegetable oil or fat.

2. Pharmaceutical preparation according to claim 1, which contains -tocopherol in an amount of up to 900% based on cyclosporin A.

3. Pharmaceutical preparation according to either of the preceding claims, which contains cyclosporin A in an amount of >10% based on the composition.

4. Pharmaceutical preparation according to claim 1 which contains ethanol or isopropanol as processing auxiliary, in an amount of up to 20%.

5. Pharmaceutical preparation according to claim 1 which contains a thickener.

6. Pharmaceutical preparation according to claim 1 which is in the form of an injection concentrate for formulations for parenteral use containing physiologically tolerable excipients.

* * * * *